United States Patent
Benz et al.

(10) Patent No.: US 12,226,545 B2
(45) Date of Patent: *Feb. 18, 2025

(54) MICRO INJECTABLE, LOW CHROMATIC ABERRATION INTRAOCULAR LENS MATERIALS

(71) Applicant: Benz Research and Development Corp., Sarasota, FL (US)

(72) Inventors: Patrick H. Benz, Sarasota, FL (US); Adam Reboul, Sarasota, FL (US)

(73) Assignee: BENZ RESEARCH AND DEVELOPMENT CORP, Sarasota, FL (US)

(*) Notice: Subject to any disclaimer, the term of this patent is extended or adjusted under 35 U.S.C. 154(b) by 43 days.

This patent is subject to a terminal disclaimer.

(21) Appl. No.: 17/726,493

(22) Filed: Apr. 21, 2022

(65) Prior Publication Data
US 2022/0249737 A1    Aug. 11, 2022

Related U.S. Application Data

(63) Continuation of application No. 16/614,322, filed as application No. PCT/US2018/032660 on May 15, 2018, now abandoned.

(60) Provisional application No. 62/506,996, filed on May 16, 2017.

(51) Int. Cl.
| | |
|---|---|
| *A61L 27/16* | (2006.01) |
| *A61L 27/50* | (2006.01) |
| *A61L 27/52* | (2006.01) |
| *C08L 33/06* | (2006.01) |
| *C08F 220/28* | (2006.01) |

(52) U.S. Cl.
CPC .............. *A61L 27/16* (2013.01); *A61L 27/52* (2013.01); *C08L 33/066* (2013.01); *A61L 2400/06* (2013.01); *A61L 2430/16* (2013.01); *C08F 220/282* (2020.02)

(58) Field of Classification Search
None
See application file for complete search history.

(56) References Cited

U.S. PATENT DOCUMENTS

| | | | |
|---|---|---|---|
| 6,365,652 B2 | 4/2002 | Gupta et al. | |
| 6,517,750 B2 | 2/2003 | Benz et al. | |
| 8,759,414 B2 | 6/2014 | Muller-Lierheim et al. | |
| 10,196,470 B2 * | 2/2019 | Benz | A61L 27/16 |
| 10,899,862 B2 * | 1/2021 | Benz | C08F 220/68 |
| 2002/0027302 A1 | 3/2002 | Benz et al. | |
| 2002/0058723 A1 | 5/2002 | Benz et al. | |
| 2002/0058724 A1 | 5/2002 | Benz et al. | |
| 2005/0131183 A1 * | 6/2005 | Benz | A61L 27/16 526/319 |
| 2006/0199929 A1 | 9/2006 | Benz et al. | |
| 2006/0276606 A1 | 12/2006 | Benz et al. | |
| 2008/0221235 A1 | 9/2008 | Benz et al. | |
| 2013/0253159 A1 * | 9/2013 | Benz | C08F 220/302 526/313 |
| 2015/0038612 A1 | 2/2015 | Mentak | |

FOREIGN PATENT DOCUMENTS

| | | |
|---|---|---|
| RU | 2557993 C1 | 7/2015 |
| RU | 2657810 C1 | 6/2018 |
| WO | WO-2007/062864 | 6/2007 |
| WO | WO-2009/120511 | 10/2009 |
| WO | WO-2012/167124 | 12/2012 |
| WO | WO-2015/161199 A1 | 10/2015 |

OTHER PUBLICATIONS

First Chinese Office Action on CN Appl. Ser. No. 201880047241.8 dated Jun. 28, 2021 (17 pages).
First Examination Report on IL Appl. Ser. No. 270644 dated Mar. 21, 2022 (8 pages).
First Examination Report on IL Appl. Ser. No. 270644 dated Oct. 4, 2021 (10 pages).
First Examination Report on IN Appl. Ser. No. 201917047540 dated Jul. 13, 2021 (5 pages).
Foreign Action other than Search Report on EP 18727986.4 dated Feb. 2, 2021 (6 pages).
International Preliminary Report on Patentability and Written Opinion on PCT Appl. Ser. No. PCT/US2018/032660 dated Nov. 28, 2019 (7 pages).
International Search Report and Written Opinion mailed Aug. 20, 2018 in PCT/US2018/032660 (10 pgs.).
Mexican Office Action on MX Appl. Ser. No. MX/a/2019/013581 dated Mar. 16, 2022 (7 pages).
Office Action dated Sep. 10, 2021 issued in related Russian Application No. 2019137719 and English translation thereof, 14 pages.
Preliminary Office Action on BR Appl. Ser. No. 112019024078-0 dated Apr. 28, 2022 (6 pages).
Second Chinese Office Action on CN Appl. Ser. No. 201880047241.8 dated Dec. 10, 2021 (15 pages).
Second Office Action on RU Patent No. 2019137719 DTD Feb. 24, 2022.
Third Office Action on CN Appl. Ser. No. 201880047241.8 dated Mar. 22, 2022 (14 pages).

* cited by examiner

*Primary Examiner* — Brian Gulledge
(74) *Attorney, Agent, or Firm* — FOLEY & LARDNER LLP

(57) ABSTRACT

The present disclosure is related to 2-(2-ethoxyethoxy)ethyl-functionalized polymers; their use in foldable intraocular lenses; and methods of making the same.

10 Claims, No Drawings

MICRO INJECTABLE, LOW CHROMATIC ABERRATION INTRAOCULAR LENS MATERIALS

CROSS-REFERENCE TO RELATED APPLICATION

This application claims priority to U.S. Provisional Application No. 62/506,996 filed on May 16, 2017, the contents of which are specifically incorporated by reference.

SUMMARY OF THE DISCLOSURE

The present disclosure is related, in part, to micro injectable, low chromatic aberration IOL materials, such as 2-(2-ethoxyethoxy)ethyl-functionalized polymers; their use in foldable intraocular lenses; and methods of making the same.

One embodiment of the disclosure relates to an intraocular lens comprising at least one copolymer comprising: a first monomeric subunit comprising a polymerized 2-(2-ethoxyethoxy)ethyl-functionalized monomer; one or more second monomeric subunits different from the first monomeric subunit; and a crosslinking agent; wherein, the first monomeric subunit comprises about 2% to about 60% of the monomeric subunits composition by weight; the copolymer has a recovery compliance elastic part ($J_e/J_{max}$) of about 90% or more and a recovery compliance viscous part ($J_v/J_{max}$) of about 10% or less; and the copolymer has (a) a dry state glass transition temperature from about 25° C. to about 75° C. and a water content at equilibrium of about 15 percent to about 25 percent based on the weight of the polymer after it is fully equilibrated in water, or (b) a glass transition temperature from about 0° C. to about 25° C. and a water content at equilibrium of less than about 6 percent based on the weight of the polymer after it is fully equilibrated in water. In some embodiments, the polymerized 2-(2-ethoxyethoxy)ethyl-functionalized monomer is selected from the group consisting of acrylate, methacrylate, acrylamide, methacrylamide, or combinations thereof. In some embodiments, the first monomeric subunit is 2-(2-ethoxyethoxy)ethyl methacrylate. In some embodiments, the one or more second monomeric subunits comprise up to about 75 wt. % of the monomeric subunits composition by weight. In some embodiments, the first monomeric subunit is about 25 wt. % to about 60 wt. %, by weight of the copolymer composition, and the one or more second monomeric subunits are about 40 wt. % to about 75 wt. %, by weight of the copolymer composition. In some embodiments, the crosslinking agent is a trifunctional methacrylate. In some embodiments, the copolymer has a glass transition temperature from about 0° C. to about 35° C. In some embodiments, the intraocular lens comprises a hydrophilic copolymer, wherein the hydrophilic copolymer comprises about 40% to about 60%, by weight of the copolymer, of 2-(2-ethoxyethoxy)ethyl methacrylate. In some embodiments, the hydrophilic polymer comprises about 40% to about 60%, by weight of the copolymer, of one or more second monomeric subunits, wherein the one or more second monomeric subunits comprise 2,3-dihydroxypropyl methacrylate. In some embodiments, the intraocular lens is hydrophilic and has an equilibrium water content ranges from about 20% to about 30% by weight of the copolymer. In some embodiments, the intraocular lens comprises a hydrophobic copolymer, wherein the hydrophobic copolymer comprises up to about 30%, by weight of the copolymer, of 2-(2-ethoxyethoxy)ethyl methacrylate. In some embodiments, the hydrophobic copolymer comprises about 70% or more, by weight of the copolymer, of one or more second monomeric subunits, wherein the one or more second monomeric subunits comprise 2-hydroxy-3-phenoxypropyl methacrylate, bromo-2-hydroxy-3-phenoxypropyl methacrylate, or combinations thereof. In some embodiments, the intraocular lens is hydrophobic and has an equilibrium water content of about 5% or less by weight of the copolymer.

Other embodiments include a composition comprising at least one copolymer comprising: a first monomeric subunit comprising a polymerized 2-(2-ethoxyethoxy)ethyl (meth)acrylate group; one or more second monomeric subunits different from the first monomeric subunit comprising a polymerized (meth)acrylate group; and a crosslinking agent; wherein the 2-(2-ethoxyethoxy)ethyl (meth)acrylate group comprises about 2% to about 60% of the monomeric subunits composition by weight.

Yet other embodiments include a method for making a composition comprising at least one copolymer comprising monomeric subunits comprising: preparing a co-monomer mixture comprising: a first monomeric subunit comprising a polymerized 2-(2-ethoxyethoxy)ethyl-functionalized monomer; one or more second monomeric subunits different from the first monomeric; and a crosslinking agent; polymerizing the co-monomer mixture by adding a photo or thermal initiator, for example, CGI 819 (photo) and Vazo type initiators; wherein: the 2-(2-ethoxyethoxy)ethyl-functionalized monomer comprises about 2% to about 60% of the monomeric subunits composition by weight. In some embodiments, the initiator is a photo initiator.

Other embodiments include an intraocular lens comprising at least one copolymer consisting essentially of: about 2% to about 60%, by weight of the copolymer, of a first monomeric subunit comprising a polymerized 2-(2-ethoxyethoxy)ethyl (meth)acrylate group; about 40% to about 98%, by weight of the copolymer, of one or more second monomeric subunits different from the first monomeric subunit; a crosslinking agent; and optionally one or more of an initiator, a UV absorber, a colorant, and an antioxidant.

DETAILED DESCRIPTION

Introduction

The present disclosure is related, in part, to 2-(2-ethoxyethoxy)ethyl-functionalized polymers; their use in foldable intraocular lenses; and methods of making the same.

2-(2-ETHOXYETHOXY)ETHYL-FUNCTIONALIZED POLYMERS 2-(2-ethoxyethoxy)ethyl-functionalized polymers are disclosed herein. In some embodiments, a 2-(2-ethoxyethoxy)ethyl-functionalized monomer that is incorporated into the polymers of the disclosure is 2-(2-ethoxyethoxy)ethyl (meth)acrylate or 2-(2-ethoxyethoxy)ethyl (meth)acrylamide. Preferably, the monomer is 2-(2-ethoxyethoxy)ethyl methacrylate.

The 2-(2-ethoxyethoxy)ethyl-functionalized monomer comprises about 2% to about 60% of the monomeric subunits composition by weight. The remaining monomer will be one or more second monomer. In some embodiments, the 2-(2-ethoxyethoxy)ethyl-functionalized monomer comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 56, 57, 57, 59, or 60% of the monomeric subunits composition by weight. The 2-(2-ethoxyethoxy)ethyl-functionalized monomer may comprise values therein between the above integers as well (e.g., about 10-60% of the monomeric subunits composition by weight). In some embodiments, the 2-(2-ethoxyethoxy) ethyl-functionalized monomer may comprises from about 2% to about 30%, about 10% to about 30%, about 25% to about 60%, about 40% to about 60%, or about 50% to about 60% of the monomeric subunits composition by weight.

In some embodiments, the 2-(2-ethoxyethoxy)ethyl-functionalized monomer and second monomer(s) form a polymer having superior viscoelastic properties. In some embodiments, the polymer has a recovery compliance elastic portion ($J_e/J_{max}$) of about 90 percent or greater. For example, the elastic portion may be about 90 percent, about 91 percent, about 92 percent, about 93 percent, about 94 percent, about 95 percent, about 96 percent, about 97 percent, about 98 percent or more. In some embodiments, the polymer has a recovery compliance viscous portion ($J_v/J_{max}$) of about 10 percent or less. For example, the viscous portion may be about 10 percent, about 9 percent, about 8 percent, about 7 percent, about 6 percent, about 5 percent, about 4 percent, about 3 percent about 2 percent, or less. These viscoelastic properties may be measured as set forth in the Examples portion herein.

In some embodiments, the polymer of the disclosure has superior viscoelastic properties as described above in combination with a desired glass transition temperature, as discussed herein. For example a desired glass transition temperature for a hydrophilic polymer or a hydrophobic polymer.

In some embodiments, the 2-(2-ethoxyethoxy)ethyl-functionalized monomer and second monomer(s) form a polymer, when formed into an IOL of the disclosure, that contains a low amount of residual unreacted monomer after polymerization. In some embodiments, the polymerization is run neat (i.e., without a solvent). In some embodiments, the copolymer contains about 1 wt. % or less, about 0.5 wt. % or less, about 0.4 wt. % or less, about 0.3 wt. % or less, about 0.2 wt. % or less, about 0.1 wt. % or less of residual unreacted monomer without being subjected to a purification step.

In some embodiments, the 2-(2-ethoxyethoxy)ethyl-functionalized monomer and second monomer(s) allow for a polymer capable of use in either a hydrophilic IOL or a hydrophobic IOL. Thus, the water content of an IOL formed from a polymer of the disclose may be about 0.5 to about 30%.

Hydrophilic Polymer

For example, hydrophilic polymer, when formed into an IOL of the disclosure, may have, e.g., a water content at equilibrium that ranges from at or about 15 percent to at or about 25 percent based on the weight of the copolymer after it is fully equilibrated in water. In other embodiments, the water content ranges from about 20 percent to about 30 percent by weight of the copolymer after it is fully equilibrated with water. For example, the water content at equilibrium may be about 15 percent, 16 percent, 17 percent, 18 percent, 19 percent, 20 percent, 21 percent, 22 percent, 23 percent, 24 percent, 25 percent or more. Due to their high water contents, the present copolymers are generally considered as hydrophilic. Generally, the lenses also have advantageous properties compared to prior lenses because they have a comparable or higher refractive index than lenses containing, e.g., Benz IOL25 (See U.S. Pat. No. 6,517,750; copolymer of 2-hydroxyethyl methacrylate and 2-ethoxyethyl methacrylate) and are more flexible, e.g., foldable, than other hydrophilic lenses that include aromatic monomeric subunits to increase the refractive index of the resulting polymer.

In some embodiments, the present hydrophilic polymer, when formed into an IOL of the disclosure, can have an Abbe value of greater 45, or 46. In some embodiments, the present polymers can have an Abbe value of 45, 46, 47, 48, or 49. In some embodiments, the present polymers can have an Abbe value of 47. The human lens has an Abbe value of about 47. A high Abbe value indicates low chromatic aberration, which is a desirable quality for IOLs. Accordingly, in certain embodiments, the IOLs of the present disclosure have an Abbe value of 45, 46, 47, 48, or 49.

In some embodiments, the Abbe value can be measured by the following formula:

Abbe Value=(Refractive Index at 589 nm−1)(Refractive Index at 486 nm−Refractive Index at 656 nm)

In some embodiments, the hydrophilic polymer, when formed into an IOL of the disclosure, contains a low amount of residual unreacted monomer after polymerization. In some embodiments, the polymerization is run neat (i.e., without a solvent). In some embodiments, the copolymer contains 2 wt. % or less, or 1 wt. % or less, 0.5 wt. % or less, 0.4 wt. % or less, 0.3 wt. % or less, 0.2 wt. % or less, 0.1 wt. % or less of residual unreacted monomer without being subjected to a purification step.

The hydrophilic polymers can be designed to have a wide range of physical characteristics. In some embodiments, a hydrophilic polymer of the present disclosure can be designed to have glass transition temperatures at or above about 25° C., for example, about 25° C. to about 75° C. or about 35° C. to about 100° C. In preferred embodiments, the glass transition temperature will be more than or about 25° C., 30° C., 35° C., 40° C., 45° C., 50° C., 55° C., 60° C., 65° C., 70° C., 75° C., 80° C., 85° C., 90° C., 85° C., 100° C. These higher glass transition temperatures may be obtained from a non-hydrated, or dry state, hydrophilic polymer. For example, a hydrophilic polymer that has not been placed, e.g., in isotonic saline or water.

The hydrophilic polymers can possess superior refractive index compared to known hydrophilic lenses, e.g., Benz IOL25 (See U.S. Pat. No. 6,517,750; copolymer of 2-Hydroxyethylmethacrylate and 2-ethoxyethylmethacrylate). In some embodiments, the refractive index of the hydrophilic polymer of the disclosure is greater than about (or about) 1.47, 1.48, 1.49 or 1.50. These refractive indices may be measured on a hydrated or non-hydrated lens.

In some embodiments, the hydrophilic polymer may comprise the 2-(2-ethoxyethoxy)ethyl-functionalized monomer in an amount up to about 60% of the monomeric subunits composition by weight. In some embodiments, 2-(2-ethoxyethoxy)ethyl-functionalized monomer may comprise about 20%, 25%, 30%, 35%, 40%, 45%, 50%, 55% or 60% of the monomeric subunits composition by weight. The monomer may comprise values in between these values as well, e.g., about 30% to about 60%, about 40% to about 60%, or about 50% to about 60% by weight of the monomeric subunits composition.

Hydrophobic Polymer

Hydrophobic polymer, when formed into an IOL of the disclosure, may have, e.g., a water content of less than or about 5 percent, or less than about 3 percent, based on the weight of the copolymer after it is fully equilibrated in water. In some embodiments, the hydrophobic polymers have a water content at equilibrium that ranges from at or about 1 percent to at or about 5 percent based on the weight of the hydrophobic polymer after it is fully equilibrated in water. In other embodiments, the water content ranges from about 2 percent to about 4 percent by weight of the copolymer after it is fully equilibrated with water.

The hydrophobic polymers can possess superior mechanical and optical properties over other materials used to make IOLs, for example an increased refractive index over the prior art, which also remain foldable, low in glistenings and high in Abbe value. The components of present embodiments can provide for a hydrophobic lens with low $T_g$, reduced glistenings and reduced stickiness providing for an IOL with desirable and reliable unfolding times, while maintaining a high refractive index.

The hydrophobic polymers can be designed to have a wide range of physical characteristics. In some instances, the present copolymers can be designed to have glass transition temperatures below at or about 35° C., below at or about 30° C., below at or about 25° C., such as from at or about −25° C. to at or about 35° C., 30° C., or 25° C., from about −5° C. to about 5° C., 10° C., 15° C., 20° C., or about 25° C., or from at or about 0° C. to at or about 15° C. In some embodiments, the glass transition temperature will be from about 0° C. to about 10° C., from about 0° C. to about 8° C., from about 0° C. to about 5° C., or from about 0° C. to about 3° C. In preferred embodiments, the glass transition temperature will be from about −5° C. to about 5° C. In preferred embodiments, the glass transition temperature will be less than about 10° C., 9° C., 8° C., 7° C., 6° C., 5° C., 4° C., 3° C., 2° C., 1° C., 0° C., −1° C., −2° C., −3° C., −4° C., or about −5° C. Glass transition temperatures referred to herein may be measured at half width at a temperature change rate of 10° C./minute, or other methods known in the art.

As the present hydrophobic polymers have been designed to be used as IOLs, they also typically have a high refractive index, which is generally above about 1.46 or above 1.50. Some of the present hydrophobic polymers can have a refractive index of 1.48 or higher. Some of the present hydrophobic polymers can have a refractive index of 1.50 or higher. In some embodiments, the hydrophobic polymers provided herein have a refractive index of 1.50, 1.51, 1.52, or 1.53.

Because the present hydrophobic polymers are hydrophobic, they can also have equilibrium water contents that are about 5 percent or less, for example 4 percent, 3 percent, 2 percent, 1 percent or less. Due to their low water contents, the present hydrophobic polymers are generally not considered hydrogels and may be considered as hydrophobic. Generally, the present hydrophobic polymers lenses also have advantageous properties compared to prior lenses because they have a comparable or higher refractive index than lenses containing silicone or p-hydroxyethyl methacrylate and are more flexible, e.g., foldable, than hydrophobic lenses that include aromatic monomeric subunits to increase the refractive index of the resulting polymer.

In some embodiments, the hydrophobic polymers provided herein have a SI value of less than 850. In some embodiments, the hydrophobic polymers provided herein have a SI value of from about 600 to about 850. In some embodiments, the hydrophobic polymers provided herein have a SI value of less than 825, 800, 775, 750, 725, 700, 675, 650, or 625 as measured on the Trattler severity index.

In some embodiments, the hydrophobic polymer may comprise the 2-(2-ethoxyethoxy)ethyl-functionalized monomer in amounts up to about 30% of the monomeric subunits composition by weight. In some embodiments, the 2-(2-ethoxyethoxy)ethyl-functionalized monomer may comprise about 5%, 10%, 15%, 20%, 25%, or 30%, of the monomeric subunits composition by weight. The monomer may comprise values in between these values as well, e.g., about 10% to about 30%, about 15% to about 30%, or about 20% to about 30% by weight of the monomeric subunits composition by weight.

Second Monomer

The second monomer(s) that are incorporated into the 2-(2-ethoxyethoxy)ethyl-functionalized polymer of the disclosure are not particularly limited. However, in a preferred embodiment, the second monomer(s), when incorporated into the polymers of the disclosure allow for use in foldable intraocular lenses. In some embodiments, the 2-(2-ethoxyethoxy)ethyl-functionalized monomer and second monomer(s) are capable of being solubilized without a solvent, and thus, are able to undergo polymerization neat (i.e., without an external solvent).

In a preferred embodiment, the second monomer(s) comprise the same reactive (meth)acrylate or (meth)acrylamide moiety as the first monomer. For example, some embodiments include 2-(2-ethoxyethoxy)ethyl methacrylate as the first monomer, and include second monomer(s) with a methacrylate moiety.

In some embodiments, the second monomer(s) do not include monomers with a vinyl reactive moiety. In other embodiments, the second monomer(s) do not include monomers containing silicon, e.g., a siloxane moiety. In other embodiments, the second monomer(s) do not include monomers containing a carbazole moiety and/or naphthyl moiety and//or anthracene moiety. In other embodiments, the second monomer(s) include less than 15, 14, 13, 12, 11, 10, 9, 8, 7, 6, 5, 4, 3, 2, or 1% of the monomeric subunits composition by weight that include a siloxane moiety and/or a carbazole moiety and/or naphthyl moiety and//or anthracene moiety.

The following provides a non-limiting example of various monomers that may alone or in combination make us the second monomer.

Second Monomer Comprising an Aryl Moiety

The hydrophobic and hydrophilic polymers of the present disclosure may include one or more monomer comprising an aryl moiety, e.g., an optionally substituted phenyl moiety. In some embodiments, the hydrophobic polymers of the present disclosure include about 50% to about 90% of incorporated monomer(s) comprising an aryl moiety (e.g., 50, 55, 60, 65, 70, 75, 80, 85 or 90% by weight of the monomeric subunits composition). The monomer may comprise values in between these values as well. In some embodiments, the hydrophilic polymers of the present disclosure may include about 5% to about 40% of incorporated monomer(s) comprising an aryl moiety (e.g., 5, 10, 15, 20, 25, 30, 35 or 40% by weight of the monomeric subunits composition. The monomer may comprise values in between these values as well. In some embodiments, the monomer comprising an aryl moiety is characterized in that a homopolymer of the monomer comprising an aryl moiety has a refractive index of at least about 1.52, e.g., about 1.52 to about 1.59 or about 1.52, 1.53, 1.54, 1.55, 1.56, 1.57, 1.58, or 1.59.

In some embodiments, the monomer comprising an aryl moiety may include one or more aryloxyalkyl moiety. For example:

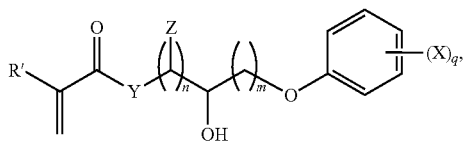

wherein R' is hydrogen or methyl, Y is O or —NR", X is Cl, Br, —CH₃, or —OCH₃, n is 1 to 6, m is 1 to 6, q is 0-5, R" is hydrogen or a $C_1$ to $C_5$ alkyl; and Z is H, OH or a halogen group. In some embodiments, q is 1 or 2, or q is 0. In other embodiments, n and m are 1 or 2 and X is Br, Z is H, and Y is O, and q is 1, 2, 3, 4, or 5, or q is 0. In some embodiments, q is 1 or 2, or q is 0. In another embodiment, the aryloxy group comprises a phenoxy group. In yet another embodiment, the aryloxy group comprises an unsubstituted phenoxy group. In another embodiment, the aliphatic carbon moiety of the second monomer is substituted with one hydroxyl group. In another embodiment, the aliphatic carbon moiety of the second monomer is a $C_3$ moiety. In another embodiment, the aliphatic carbon moiety of the second monomer is represented by —CH(Br)—CHOH—CH₂—. Finally, the side group of the monomer comprising an aryl moiety, in one embodiment, comprises —CH(Br)—CHOH—CH₂—OPh, wherein OPh is an unsubstituted phenoxy group.

Examples of some specific hydroxy and halogen-substituted aryloxyalkyl methacrylate, hydroxy and halogen-substituted aryloxyalkyl acrylate, hydroxy and halogen-substituted aryloxyalkyl methacrylamide and hydroxy and halogen-substituted aryloxyalkyl acrylamide monomeric subunits useful for forming the copolymers, but are not limited to, 2-bromo-2-hydroxy-3-phenoxypropyl acrylate, 3-bromo-2-hydroxy-3-phenoxypropyl acrylate, 4-bromo-2-hydroxy-3-phenoxypropyl acrylate, 2-bromo-2-hydroxy-3-phenoxypropyl methacrylate, 3-bromo-2-hydroxy-3-phenoxypropyl methacrylate, 4-bromo-2-hydroxy-3-phenoxypropyl methacrylate, 2-bromo-2-hydroxy-3-phenoxypropyl acrylamide, 3-bromo-2-hydroxy-3-phenoxypropyl acrylamide, 4-bromo-2-hydroxy-3-phenoxypropyl acrylamide, and/or 2-bromo-2-hydroxy-3-phenoxypropyl methacrylamide, 3-bromo-2-hydroxy-3-phenoxypropyl methacrylamide, or 4-bromo-2-hydroxy-3-phenoxypropyl methacrylamide. In some embodiments, the monomer comprising an aryl moiety comprises bromo-2-hydroxy-3-phenoxypropyl methacrylate (BrHPPMA), e.g., in an amount of up to 30% by weight. It is understood that the above examples may alternatively have a different reactive moiety, e.g., a different one of reactive (meth) acrylate or (meth)acrylamide moiety, which are also within the present disclosure.

Examples of some specific hydroxy-substituted aryloxyalkyl methacrylate, hydroxy substituted aryloxyalkyl acrylate, hydroxy-substituted aryloxyalkyl methacrylamide and hydroxy-substituted aryloxyalkyl acrylamide monomeric subunits useful for forming the copolymers, but are not limited to, 2-hydroxy-3-phenoxypropyl acrylate, 2-hydroxy-3-phenoxypropyl methacrylate, 2-hydroxy-3-phenoxypropyl acrylamide, and/or 2-hydroxy-3-phenoxypropyl methacrylamide. In some embodiments, the first monomer comprises 2-hydroxy-3-phenoxypropyl methacrylate (HPPMA). It is understood that the above examples may alternatively have a different reactive moiety, e.g., a different one of reactive (meth)acrylate or (meth)acrylamide moiety, which are also within the present disclosure.

Second Monomer Comprising a Hydrophilic Moiety

The hydrophobic and hydrophilic polymers of the present disclosure may include one or more monomer comprising a hydrophilic moiety, e.g., an optionally substituted aliphatic moiety or alkoxy moiety. In some embodiments, the hydrophobic polymers of the present disclosure include about 0% to about 20% of incorporated monomer(s) comprising a hydrophilic moiety (e.g., 0, 5, 10, 15, or 20% by weight of the monomeric subunits composition). The monomer may comprise values in between these values as well. In some embodiments, the hydrophilic polymers of the present disclosure may include about 10% to about 50% of incorporated monomer(s) comprising an aryl moiety (e.g., 10, 15, 20, 25, 30, 35, 40, 40 or 50% by weight of the monomeric subunits composition. The monomer may comprise values in between these values as well.

In some embodiments, the monomer comprising a hydrophilic moiety may include a C1-C5 alkyl moiety and one or more hydroxyl substituents, e.g. 1, 2, 3, 4 hydroxyl substituent(s). In some embodiments, the at least one carbon moiety comprising at least two hydroxyl substituents is a C2-C5 alkyl moiety comprising or consisting of 2, 3, 4 hydroxyl substituents. Examples include but are not limited to dihydroxypropyl (e.g., 2,3-dihydroxypropyl), dihydroxybutyl (e.g., 2,3-dihydroxybutyl, 2,4-dihydroxybutyl, 3,4-dihydroxybutyl), and the like. In some embodiments, the second monomer includes dihydroxypropyl methacrylate (or glycerol methacrylate (GMA)). It is understood that the above examples may alternatively have a different reactive moiety, e.g., a different one of reactive (meth)acrylate or (meth)acrylamide moiety, which are also within the present disclosure.

In other embodiments, the monomer comprising a hydrophilic moiety includes a monomeric subunit comprising a polymerized (meth)acrylamide group. Examples include but are not limited to N,N-dimethyl(meth)acrylamide, ethoxyethyl(meth)acrylamide, acrylamide, dihydroxypropyl acrylamide, hydroxy ethyl acrylamide, hydroxy methyl acrylamide. In other embodiments, the monomer comprising a hydrophilic moiety includes a monomeric subunit comprising a polymerized (meth)acrylamide group also includes a C1-C5 alkyl moiety. In some embodiments, the monomer comprising a hydrophilic moiety includes a monomeric subunit comprising a polymerized (meth)acrylamide group also includes a C1-C5 alkyl moiety and one or more hydroxyl substituents, e.g. 1, 2, 3, 4 hydroxyl substituent(s). It is understood that the above examples may alternatively have a different reactive moiety, e.g., a different one of reactive (meth)acrylate or (meth)acrylamide moiety, which are also within the present disclosure.

In some embodiments, the monomer comprising a hydrophilic moiety may include one or more polyalkylene glycol alkylether acrylate and/or polyalkylene glycol alkylether methacrylate monomeric subunits including of higher molecular weight. Examples of polyalkylene glycol alkylether acrylate and/or polyalkylene glycol alkylether methacrylate include, for example, polyethylene glycol monomethyl ether methacrylate monomeric subunits of varying molecular weight. In some embodiments, the monomer comprising a hydrophilic moiety may be polyethylene glycol monomethyl ether methacrylate (200 PEG MW) or polyethylene glycol monomethyl ether methacrylate (400 PEG MW). In another embodiment, polyethylene glycol monomethyl ether methacrylate of other molecular weights may be used. Other polyethylene glycol monomethyl ether methacrylate compositions may be used. It is to be understood that any reference to the molecular weight of the PEG subunit refers to average molecular weight. Accordingly, 200 PEG MW refers to a polyethylene glycol monomethyl ether methacrylate that has an average molecular weight of about 200. Similarly, 400 PEG MW refers to a polyethylene glycol monomethyl ether methacrylate with an average molecular weight of about 400. 200 PEG MW and 400 PEG MW are commercially available as having an average molecular weight of about 200 or 400 respectively. In some embodiments, average molecular weight refers to a weight average molecular weight. In some embodiments, the average molecular weight is +/−5 or 10% of the value, or +/−less than 5, 10, 25, or 30 g/mol of the recited molecular weight. It is understood that the above examples may alternatively have a different reactive moiety, e.g., a different one of reactive (meth)acrylate or (meth)acrylamide moiety, which are also within the present disclosure.

In some embodiments, the monomer comprising a hydrophilic moiety may include one or more subunits including alkoxyalkyl methacrylate and/or alkoxyalkyl acrylate monomeric subunits. In some embodiments, the monomer comprising a hydrophilic moiety comprises a (meth)acrylate group and containing one alkoxyalkyl side group. Alkoxyalkyl methacrylate monomeric subunits can be represented by the formula $R_5$—O—$R_6$-MA where $R_5$ and $R_6$ are alkyl groups and "MA" is methacrylate. Alkoxyalkyl acrylate monomeric subunits can be represented by the formula $R_7$—O—$R_8$-A where $R_7$ and $R_8$ are alkyl groups and "A" is acrylate. Both alkoxyalkyl methacrylates and alkoxyalkyl acrylates are ester-containing monomer compounds as will be recognized by those skilled in the art. In some embodiments, $R_5$ to $R_8$ can be independently selected from alkyl groups having 1 to 5 carbon atoms and in some embodiments 1, 2, 3, 4, or 5 carbon atoms. With respect to $R_6$ it will be understood that the alkyl group is bonded to the O of the $R_5$—O group and is also bonded to the O atom of the MA group. Similarly, with respect to $R_8$, it will be understood that the alkyl group is bonded to the O of the $R_7$—O group and is also bonded to the O atom of the A group. Alkyl groups that may be used in accordance with the embodiments herein include straight chain alkyl groups, including but not limited to methyl, ethyl, propyl, butyl, and pentyl groups. Alkyl groups may also include branched chain isomers of straight chain alkyl groups including, but not limited to, the following, which are provided by way of example only: —$CH(CH_3)_2$, —$CH(CH_3)(CH_2CH_3)$, —$CH(CH_2CH_3)_2$, —$C(CH_3)_3$, and the like. In some embodiments, the alkoxyalkyl methacrylate or alkoxyalkyl acrylate is selected where $R_5$, to $R_8$ have 1, 2, 3, or 4 carbon atoms. Examples of some specific alkoxyalkyl methacrylate and alkoxyalkyl acrylate monomeric subunits useful for forming the copolymers of the embodiments herein include, but are not limited to, methoxyethyl methacrylate, ethoxyethyl methacrylate, propoxyethyl methacrylate, butoxymethyl methacrylate, methoxypropyl methacrylate, ethoxypropyl methacrylate, propoxypropyl methacrylate, butoxypropyl methacrylate, methoxybutyl methacrylate, ethoxybutyl methacrylate, propoxybutyl methacrylate, butoxybutyl methacrylate, methoxyethyl acrylate, ethoxyethyl acrylate, propoxyethyl acrylate, butoxymethyl acrylate, methoxypropyl acrylate, ethoxypropyl acrylate, propoxypropyl acrylate, butoxypropyl acrylate, methoxybutyl acrylate, ethoxybutyl acrylate, propoxybutyl acrylate, and butoxybutyl acrylate. In some preferred embodiments, the copolymer includes ethoxyethyl methacrylate (EOEMA). It is understood that the above examples may alternatively have a different reactive moiety, e.g., a different one of reactive (meth) acrylate or (meth)acrylamide moiety, which are also within the present disclosure.

Hence, a particularly preferred embodiment provides an intraocular lens, wherein the alkoxyalkyl group is a $C_3$ to $C_{12}$ group. In one embodiment, the alkoxyalkyl group comprises a single oxygen atom. In some embodiments, the alkoxyalkyl group is not a repeating alkoxyalkyl group. In a specific embodiment, the alkoxyalkyl group is 2-ethoxyethyl. It is understood that the above examples may alternatively have a different reactive moiety, e.g., a different one of reactive (meth)acrylate or (meth)acrylamide moiety, which are also within the present disclosure.

In some embodiments, an alkoxyalkyl methacrylate and/or alkoxyalkyl acrylate monomeric subunits are utilized in the copolymer disclosed herein to produce copolymers with a higher glass transition temperature.

In some embodiments, the monomer comprising a hydrophilic moiety may include HEA, and/or lauryl (meth)acrylate. It is understood that the above examples may alternatively have a different reactive moiety, e.g., a different one of reactive (meth)acrylate or (meth)acrylamide moiety, which are also within the present disclosure.

In some embodiments, the hydrophobic polymer as described herein includes the one or more second monomer(s) in an amount of about 40%, about 50%, about 60%, about 70%, about 75%, about 80%, or about 90% or more by weight of the monomeric subunits composition. In some embodiments, the hydrophobic monomer includes the one or more second monomer(s) from about 40% to about 98%, about 40% to about 75%, about 50% to about 95%, about 60% to about 90%, about 70% to about 85% by weight of the monomeric subunits composition. In some embodiments, the hydrophobic polymer may comprise 70% or more of the second monomer(s) by weight of the monomeric subunits composition, where the second monomer(s) includes HPPMA, BrHPPMA, or combinations thereof.

In some embodiment, the hydrophilic polymer as described herein includes the one or more second monomer(s) from about 40% to about 60% by weight of the monomeric subunits composition. In some embodiments, the hydrophilic polymer includes the second monomer(s) from about 40% to about 60%, about 40% to about 55%, about 40% to about 50% by weight of the monomeric subunits. In some embodiments, the hydrophilic polymer includes the second monomer(s) from about 40% to about 50% by weight of the monomeric subunits composition, where the second monomer(s) includes GMA, HPPMA, BrHPPMA.

Crosslinking Agent

The 2-(2-ethoxyethoxy)ethyl-functionalized polymers comprise a crosslinking agent. For example, bi- or tri-functional crosslinking agents can be used to form the crosslinked subunits. However, other di- or multi-functional crosslinking agents known in the art may also be employed instead, or in addition to the bi- or tri-functional crosslinking agents.

The copolymers can be prepared using conventional polymerization techniques known to those in the field of polymer chemistry. Crosslinkers may be employed in the polymerization reaction. For example, any crosslinking or difunctional monomer, can be used in effective amounts to give the desired crosslinking density. For example, in a concentration range of 0 to about 10 percent, such as about 0.01 to about 4 percent, or in some embodiments from 0.5 to 3 percent by weight, based on the weight of the polymer. Examples of suitable crosslinking agents include di-olefinic functional component, ethylene glycol dimethacrylate (EGDMA), diethylene glycol dimethacrylate ("DE-GDMA"), triethylene glycol dimethacrylate, and the like. Generally, crosslinkers help to enhance the resulting copolymer's dimensional stability. It is understood that the above examples may alternatively have a different reactive moiety, e.g., a different one of reactive (meth)acrylate or (meth)acrylamide moiety, which are also within the present disclosure.

In some embodiments, the compositions include one or more crosslinker with three or more polymerizable functionalities (a multi-functional crosslinking agent). An example of a multi-functional crosslinking agent includes, but is not limited to, trimethylol propane trimethacrylate (TMPTMA). The analogous acrylate crosslinking agents, for example, trimethylol propane triacrylate, may also be utilized in place of any of their methacrylate analogs or in combination with the methacrylate analogs. Some embodiments include two or more tri-functional crosslinking agents or a multi-functional crosslinking agent and a di-functional crosslinking agent known in the art or incorporated herein by reference, such as for example EGDMA or DEGDMA. Therefore, in some embodiments, the copolymer compositions include EGDMA, DEGDMA, and/or TMPTMA. In some such embodiments, the amount of EGDMA and/or TMPTMA ranges from about 0.5 to about 5 (e.g., about 2 to about 3 or about 2.5 to about 3) percent by weight based on the weight of the dry copolymer. In the present copolymers, the total quantity of the one or more of the crosslinking monomeric subunit will make up a minority of the copolymer. For example, in some embodiments, the total quantity of the combined amounts of incorporated crosslinking monomeric subunit ranges from about 0.5 percent to 3.0 percent by weight based on the total weight of the copolymer. In some embodiments, the crosslinking monomeric subunit may include about 0.5-1.0 percent, about 0.5-1.5 percent, about 0.5-2.0 percent, or about 0.5-2.5 percent by weight of the copolymer. In some embodiments, the crosslinking monomeric subunit may include about 0.5 percent, about 0.6 percent, about 0.7 percent, about 0.8 percent, about 0.9 percent, about 1.0 percent, about 1.1 percent, about 1.2 percent, about 1.3 percent, about 1.4 percent, about 1.5 percent, about 1.6 percent, about 1.7 percent, about 1.8 percent, about 1.9 percent, about 2.0 percent, about 2.1 percent, about 2.2 percent, about 2.3 percent, about 2.4 percent, about 2.5 percent, about 2.6 percent, about 2.7 percent, about 2.8 percent, about 2.9 percent, or about 3.0 percent by weight of the copolymer. In some embodiments, the crosslinking monomeric subunit may include about 2.74 percent by weight of the copolymer.

In one embodiment, the only crosslinking agent used is a trifunctional crosslinking agent such as a trifunctional methacrylate crosslinking agent.

Additional Components

Also, if desired an initiator can be used in the polymerization. Initiators are not particularly limited, and include initiator such as azo derivatives, like 2,2-azobis (2,4-dimethylvaleronitrile) and propanenitrile, 2-methyl, 2,2'-azobis. The initiator may also be a photo initiator, a thermal initiator, or other type of initiator as recognized by one skilled in the art. In some embodiments, the photo initiator is CGI 819. The initiator is used in an amount effective for initiation purposes, and is generally present from about 0.01 to 1.0 percent by weight, based on the weight of the polymer.

The copolymers of the present embodiments can also include additional monomers, such as, but not limited to, monomers that impart ultraviolet (UV) absorption to the polymer and/or monomers that impart absorption to the lens, such as blue light-blocking. UV absorbing monomers are typically aromatic compounds with olefinic functionality. The advantageous UV absorbing compounds can be added prior to polymerization for incorporation into the resultant polymer, as is well known in the art. The UV absorber should preferably be capable of polymerization into the lens matrix so as to be stable under physiological conditions. Any monomer copolymerizable with the described monomeric subunits can optionally be used, so long as such monomer does not materially or adversely affect the basic characteristics of the intraocular lens. Examples of useful additional monomers that can be used are described in U.S. Pat. No. 5,326,506, hereby incorporated by reference, directed to a composite intraocular lens. Additionally, aryl-substituted triazole compounds, such as for example, tris-aryl triazole compounds described in U.S. Pat. No. 6,365,652, may be used in at low concentrations to achieve desired UV absorbing properties. Such optional additional monomers, preferably are present in a total amount of not more than 10 weight percent, generally less than 5 weight percent, based on the total weight of the polymer.

In some embodiments, the present disclosure does not include that disclosed in PCT/US2017/032698 and U.S. Ser. No. 15/586,890. In other embodiments, it does incorporate this disclosure. For example, in some embodiments, the polymers or IOLs of the present disclosure do not include an intraocular lens or polymer comprising at least one copolymer comprising: (a) a first monomeric subunit comprising a polymerized (meth)acrylate group and at least one alkoxyalkoxyalkyl side group, (b) a second monomeric subunit different from the first monomeric subunit comprising a polymerized (meth)acrylate group, at least one side group comprising (i) an aryloxy moiety comprising at least one halogen, and (ii) an aliphatic carbon moiety linking the aryloxy moiety with the polymerized (meth)acrylate group, wherein the aliphatic carbon moiety comprises at least one hydroxyl substituent, (c) a third monomeric subunit different from the first and second monomeric subunits comprising a polymerized (meth)acrylate group, at least one side group comprising (i) an aryloxy moiety, and (ii) an aliphatic carbon moiety linking the aryloxy moiety with the polymerized (meth)acrylate group, wherein the aliphatic carbon moiety comprises at least one hydroxyl substituent, (d) optionally a fourth monomeric subunit different from the first, second, and third monomeric subunits comprising a polymerized acrylate or (meth)acrylate group, and at least one alkylene oxide side group and (e) optionally a fifth monomeric subunit different from the first, second, third, and fourth monomeric subunits comprising a polymerized (meth)acrylate group and at least one alkoxyalkyl side group. In some embodiments, the polymers or IOLs of the present disclosure do not include a hydrophilic intraocular lens comprising at least one copolymer comprising: (a) a first monomeric subunit comprising (i) a polymerized (meth)acrylate group and an aliphatic carbon moiety comprising at least two hydroxyl substituent or (ii) a polymerized (meth)acrylamide group, (b) a second monomeric subunit different from the first monomeric subunit comprising a polymerized (meth)acrylate group, at least one side group comprising (i) an aryloxy moiety comprising at least one halogen, and (ii) an aliphatic carbon moiety linking the aryloxy moiety with the polymerized (meth)acrylate group, wherein the aliphatic carbon moiety optionally comprises at least one hydroxyl substituent, (c) a third monomeric subunit different from the first and second monomeric subunits comprising a polymerized (meth)acrylate group and at least one alkoxyalkoxyalkyl side group.

Methods of Making Composition
Formation of Intraocular Lens

The intraocular lenses of the present embodiments may be formed by methods known in the art. For example, in an exemplary process, the monomeric subunits that form the copolymer are polymerized into a polymer rod, polymer blanks or discs are formed from the rod, and then the blanks are cut, for example, by a lathe into the intraocular lens. The rods can be made by a procedure which begins with polymerizing, in a mold, such as in a tubular or cylindrical mold, a mixture of initiator and monomeric subunits, to form an optically clear soft lens body. As discussed above, it may be desirable to incorporate cross-linking materials and ultraviolet-absorbing compounds during polymerization or into the resultant polymer matrix. In some embodiments, the polymer rods are then cut and ground or otherwise machined, into blanks of the desired diameter and thickness by lathe cutting and machine milled at temperatures below the $T_g$ into an intraocular lens.

Generally, the composite material rod is lathe cut or ground to a diameter 0.5 to 2.0 mm thicker than the required distance from the center of the lens body to the furthest edge of the legs or haptics. This rod is then cut into blanks of uniform thickness. The blanks are ground and lapped to a diameter and thickness suitable for lathe cutting and machine milling in the conventional manner into the intraocular lens of the present embodiments. Because the present copolymers may have low glass transition temperatures, the rod or blanks may require cooling below $T_g$ prior to and/or during cutting, lathing and/or milling.

One having ordinary skill in the field of intraocular lens manufacturing, from a review of the present specification, can make intraocular lenses using the general knowledge in the art on intraocular lens manufacture and the process of cryogenic machining.

Intraocular lenses can also be made by molding the present copolymer to form all or part of the optic portion of the lens. For example, the present copolymer can be polymerized in a mold by a liquid mixture of monomeric subunits and additional components, to form an optically clear soft lens body. These molding methods can involve molding the optics on one half of the lens, such as the anterior or posterior portion, or fully molding the lens. When only half of the optic portion of the lens is formed in the mold then the second side optics can be machined, for example as discussed above. In either of these embodiments, additional material can be molded to allow machining of various haptic designs. The copolymer may be optionally molded in the form of a preformed lens as known in the art as a universal blank.

All references cited herein are incorporated by reference in their entirety, including hydrophobic and hydrophilic foldable IOLs described in the art in, for example, U.S. Pat. Nos. 7,947,796, 7,387,642, 7,067,602, 6,517,750 and 6,267,784 each of which is hereby incorporated by reference in its entirety. See also, for example, U.S. Patent Publication Nos. 2013/0253159, 2008/0221235, 2006/0276606, 2006/0199929, 2005/0131183, 2002/0058724, 2002/0058723 and 2002/0027302, along with WO/2015/161199. Finally, PCT/US2017/032698 and U.S. Ser. No. 15/586,890.

As used herein, the term "(meth)acrylate" refers to acrylic or methacrylic acid, esters of acrylic or methacrylic acid, and salts, amides, and other suitable derivatives of acrylic or methacrylic acid, and mixtures thereof. Illustrative examples of suitable (meth)acrylic monomers include, without limitation, the following methacrylate esters: methyl methacrylate, ethyl methacrylate, n-propyl methacrylate, n-butyl methacrylate (BMA), isopropyl methacrylate, isobutyl methacrylate, n-amyl methacrylate, n-hexyl methacrylate, isoamyl methacrylate, 2-hydroxyethyl methacrylate, 2-hydroxypropyl methacrylate, N,N-dimethylaminoethyl methacrylate, N,N-diethylaminoethyl methacrylate, t-butylaminoethyl methacrylate, 2-sulfoethyl methacrylate, trifluoroethyl methacrylate, glycidyl methacrylate, benzyl methacrylate, allyl methacrylate, 2-n-butoxyethyl methacrylate, 2-chloroethyl methacrylate, sec-butyl-methacrylate, tert-butyl methacrylate, 2-ethylbutyl methacrylate, cinnamyl methacrylate, crotyl methacrylate, cyclohexyl methacrylate, cyclopentyl methacrylate, 2-ethoxyethyl methacrylate, furfuryl methacrylate, hexafluoroisopropyl methacrylate, methallyl methacrylate, 3-methoxybutyl methacrylate, 2-methoxybutyl methacrylate, 2-nitro-2-methylpropyl methacrylate, n-octylmethacrylate, 2-ethylhexyl methacrylate, 2-phenoxyethyl methacrylate, 2-phenylethyl methacrylate, phenyl methacrylate, propargyl methacrylate, tetrahydrofurfuryl methacrylate and tetrahydropyranyl methacrylate. Example of suitable acrylate esters include, without limitation, methyl acrylate, ethyl acrylate, n-propyl acrylate, isopropyl acrylate, n-butyl acrylate (BA), n-decyl acrylate, isobutyl acrylate, n-amyl acrylate, n-hexyl acrylate, isoamyl acrylate, 2-hydroxyethyl acrylate, 2-hydroxypropyl acrylate, N,N-dimethylaminoethyl acrylate, N,N-diethylaminoethyl acrylate, t-butylaminoethyl acrylate, 2-sulfoethyl acrylate, trifluoroethyl acrylate, glycidyl acrylate, benzyl acrylate, allyl acrylate, 2-n-butoxyethyl acrylate, 2-chloroethyl acrylate, sec-butyl-acrylate, tert-butyl acrylate, 2-ethylbutyl acrylate, cinnamyl acrylate, crotyl acrylate, cyclohexyl acrylate, cyclopentyl acrylate, 2-ethoxyethyl acrylate, furfuryl acrylate, hexafluoroisopropyl acrylate, methallyl acrylate, 3-methoxybutyl acrylate, 2-methoxybutyl acrylate, 2-nitro-2-methylpropyl acrylate, n-octylacrylate, 2-ethylhexyl acrylate, 2-phenoxyethyl acrylate, 2-phenylethyl acrylate, phenyl acrylate, propargyl acrylate, tetrahydrofurfuryl acrylate and tetrahydropyranyl acrylate.

Applications

One application is lens, including lens adapted for the human eye, including IOLs.

Additional embodiments include methods of increasing the viscoelastic properties of an IOL by incorporating a 2-(2-ethoxyethoxy)ethyl-functionalized monomer of the present disclosure into an IOL polymer composition. The intraocular lenses of the embodiments may be inserted into the eye in known manners. For example, the intraocular lens may be folded prior to insertion into the eye by small, thin forceps of the type typically used by ophthalmic surgeons. After the lens is in the targeted location, it is released to unfold. As is well known in the art, typically the lens that is to be replaced is removed prior to insertion of the intraocular lens. The intraocular lens of the present embodiments can be made of a generally physiologically inert soft polymeric material that is capable of providing a clear, transparent, refractive lens body even after folding and unfolding. In some embodiments, the foldable intraocular lens of the present embodiments can be inserted into any eye by injection whereby the mechanically compliant material is folded and forced through a small tube such as a 1 mm to 3 mm inner diameter tube. In one embodiment the small tube has an inner diameter of approximately 2.0 or 1.9 or 1.8 or 1.7 or 1.6 or 1.5 mm or less. In one embodiment the inner diameter is approximately 1.4 to 2.0 mm. In one embodiment, the inner diameter is approximately 1.8 mm, in another it is 1.6 mm. In one embodiment, the finished IOL lens is microinjectable (e.g. able to be injected through a small tube that has an inner diameter of approximately 1.8 mm or 1.6 mm).

Working Examples

EOEOEMA and EOEOEA homopolymers

EOEOEMA and EOEOEA homopolymers were formed according to the following parameters. The residual contents and water content were measured.

| Component | Wt % | Cure | Residuals | EWC |
|---|---|---|---|---|
| EOEOEMA | 100 | 0.15 mW for 60 min @45 C. 3.0 mW for 10 min @75 C. | 0.443% | 6.5 |
| EOEOEA | 100 | 0.15 mW for 60 min @45 C. 3.0 mW for 10 min @75 C. | 1.142% | 8.5 |

Stress Relaxation

Stress relaxation measurements for hydrophilic and hydrophobic polymer samples of the present technology were performed as described herein. Each sample is placed on the bottom plate of an oscillatory rheometer (Anton Paar MCR-301). The top plate is brought into contact with the sample and the desired normal force is applied to reduce slippage. The sample is allowed to equilibrate for 5 min before the shear stress is applied. The shear stress is applied for 300 s and the strain is recorded with time. The stress is released and the sample is allowed to recover for 600 s. The elastic ($J_e/J_{max}$) and viscous ($J_v/J_{max}$) portions of the recovery compliance were calculated.

Hydrophobic Sample: Strain Measurement Taken in the Dry State
Sample thickness: 1.0 mm
Sample diameter: 12.0 mm
Rheometer top plate diameter: 12.0 mm
Temperature: 25° C.
Normal Force=1 N
Shear Stress=500 Pa for 300 s
Shear Stress Relaxation=0 Pa for 600 s
Hydrophilic Sample: Strain Measurement Taken at Full Hydration in Saline
Sample thickness: 1.0 mm
Sample diameter: 12.0 mm
Rheometer top plate diameter: 12.0 mm
Temperature: 25° C.
Normal Force=5 N
Shear Stress=500 Pa for 300 s
Shear Stress Relaxation=0 Pa for 600 s

What is claimed is:

1. An intraocular lens comprising at least one copolymer comprising:
    a first monomeric subunit comprising a polymerized 2-(2-ethoxyethoxy)ethyl-functionalized monomer;
    one or more second monomeric subunits different from the first monomeric subunit; and
    a crosslinking agent;
    wherein,
        the first monomeric subunit comprises about 25% to about 60% of the monomeric subunits composition by weight;
        the copolymer has a recovery compliance elastic part ($J_e/J_{max}$) of about 90% or more and a recovery compliance viscous part ($J_v/J_{max}$) of about 10% or less;
        the copolymer exhibits a dry state glass transition temperature from about 25° C. to about 75° C. and a water content at equilibrium of about 15 percent to about 25 percent based on the weight of the polymer after it is fully equilibrated in water;
        the first monomeric subunit is 2-(2-ethoxyethoxy) ethyl methacrylate;
        the one or more second monomeric subunits comprise 2,3-dihydroxypropyl methacrylate, 2-hydroxy-3-phenoxypropyl methacrylate, bromo-2-hydroxy-3-phenoxypropyl methacrylate, or a combination of any two or more thereof; and
        the one or more second monomeric subunits are 40 wt. % to 75 wt. %, by weight of the copolymer composition.

2. The intraocular lens of claim 1, wherein the crosslinking agent is a trifunctional methacrylate.

3. The intraocular lens of claim 1, wherein the intraocular lens comprises a hydrophilic copolymer, wherein the hydrophilic copolymer comprises about 40% to about 60%, by weight of the copolymer, of 2-(2-ethoxyethoxy)ethyl methacrylate.

4. The intraocular lens of claim 3, wherein the hydrophilic polymer comprises about 40% to about 60%, by weight of the copolymer, of one or more second monomeric subunits, wherein the one or more second monomeric subunits comprise 2,3-dihydroxypropyl methacrylate.

5. The intraocular lens of claim 1, wherein the intraocular lens comprises a hydrophobic copolymer, wherein the hydrophobic copolymer comprises up to about 30%, by weight of the copolymer, of 2-(2-ethoxyethoxy)ethyl methacrylate.

6. The intraocular lens of claim 5, wherein the hydrophobic copolymer comprises about 70% or more, by weight of the copolymer, of one or more second monomeric subunits, wherein the one or more second monomeric subunits comprise 2-hydroxy-3-phenoxypropyl methacrylate, bromo-2-hydroxy-3-phenoxypropyl methacrylate, or combinations thereof.

7. An intraocular lens comprising at least one copolymer consisting essentially of:
    about 25% to about 60%, by weight of the copolymer, of a first monomeric subunit comprising a polymerized 2-(2-ethoxyethoxy)ethyl (meth)acrylate group;
    about 40% to about 75%, by weight of the copolymer, of one or more second monomeric subunits comprising 2-hydroxy-3-phenoxypropyl methacrylate, bromo-2-hydroxy-3-phenoxypropyl methacrylate, or a combination of any two or more thereof; a crosslinking agent; and
    optionally one or more of an initiator, a UV absorber, a colorant, and an antioxidant; and
    the copolymer has a recovery compliance elastic part $J_e/J_{max}$ of 90% or more and a recovery compliance viscous part $J_v/J_{max}$ of 10% or less; and
    the copolymer exhibits a dry state glass transition temperature from about 25° C. to about 75° C. and a water content at equilibrium of about 15 percent to about 25 percent based on the weight of the polymer after it is fully equilibrated in water.

8. A composition comprising at least one copolymer comprising:
    a first monomeric subunit comprising a polymerized 2-(2-ethoxyethoxy) ethyl (meth) acrylate group;
    one or more second monomeric subunits different from the first monomeric subunit, the one or more second monomeric subunits comprising 2,3-dihydroxypropyl methacrylate, 2-hydroxy-3-phenoxypropyl methacrylate, bromo-2-hydroxy-3-phenoxypropyl methacrylate, or a combination of any two or more thereof; and
a crosslinking agent;
wherein:
   the 2-(2-ethoxyethoxy) ethyl (meth) acrylate group comprises about 25% to about 60% of the monomeric subunits composition by weight;
   the copolymer has a recovery compliance elastic part $J_e/J_{max}$ of 90% or more and a recovery compliance viscous part $J_v/J_{max}$ of 10% or less; and
   the copolymer exhibits a dry state glass transition temperature from about 25° C. to about 75° C. and a water content at equilibrium of about 15 percent to about 25 percent based on the weight of the polymer after it is fully equilibrated in water.

9. A method for making a composition comprising at least one copolymer comprising monomeric subunits comprising:
preparing a co-monomer mixture comprising:
   a first monomeric subunit comprising a polymerized 2-(2-ethoxyethoxy) ethyl-functionalized monomer;
   one or more second monomeric subunits different from the first monomeric subunit, the one or more second monomeric subunits comprising 2,3-dihydroxypropyl methacrylate, 2-hydroxy-3-phenoxypropyl methacrylate, bromo-2-hydroxy-3-phenoxypropyl methacrylate, or a combination of any two or more thereof; and
a crosslinking agent;
polymerizing the co-monomer mixture by adding a photo or thermal initiator;
wherein:
   the 2-(2-ethoxyethoxy) ethyl-functionalized monomer comprises about 2% to about 60% of the monomeric subunits composition by weight;
   the copolymer has a recovery compliance elastic part $J_e/J_{max}$ of 90% or more and a recovery compliance viscous part $J_v/J_{max}$ of 10% or less; and
   the copolymer exhibits a dry state glass transition temperature from about 25° C. to about 75°° C. and a water content at equilibrium of about 15 percent to about 25 percent based on the weight of the polymer after it is fully equilibrated in water.

10. The method of claim 9, wherein the photo initiator is added.

* * * * *